(12) United States Patent
Yakabe

(10) Patent No.: US 7,088,112 B2
(45) Date of Patent: *Aug. 8, 2006

(54) SENSOR CAPACITY SENSING APPARATUS AND SENSOR CAPACITY SENSING METHOD

(75) Inventor: Masami Yakabe, Tokyo (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/488,598

(22) PCT Filed: Sep. 6, 2002

(86) PCT No.: PCT/JP02/09083

§ 371 (c)(1),
(2), (4) Date: Oct. 4, 2004

(87) PCT Pub. No.: WO03/023417

PCT Pub. Date: Mar. 20, 2003

(65) Prior Publication Data

US 2005/0036271 A1    Feb. 17, 2005

(30) Foreign Application Priority Data

Sep. 6, 2001    (JP)    ............... 2001-270800

(51) Int. Cl.
G01R 27/26    (2006.01)
(52) U.S. Cl. ............................. 324/658; 324/686
(58) Field of Classification Search ............... 324/658, 324/686
See application file for complete search history.

(56) References Cited

U.S. PATENT DOCUMENTS

| | | | | |
|---|---|---|---|---|
| 5,744,968 A | * | 4/1998 | Czarnocki et al. | 324/608 |
| 6,145,384 A | * | 11/2000 | Ikeda et al. | 73/780 |
| 6,373,264 B1 | * | 4/2002 | Matsumoto et al. | 324/667 |
| 6,375,714 B1 | * | 4/2002 | Rump et al. | 95/3 |
| 6,756,790 B1 | * | 6/2004 | Yakabe et al. | 324/649 |

FOREIGN PATENT DOCUMENTS

| | | |
|---|---|---|
| DE | 30 07 426 A1 | 9/1981 |
| JP | 09-280806 | 10/1997 |
| JP | 2001-324520 | 11/2001 |
| JP | 2002-022785 | 1/2002 |
| JP | 2002-022786 | 1/2002 |
| JP | 2002-157671 | 5/2002 |
| WO | WO 96/41118 | 12/1996 |
| WO | WO 99/38019 | 7/1999 |

* cited by examiner

*Primary Examiner*—Anjan Deb
*Assistant Examiner*—Jeff Natalini
(74) *Attorney, Agent, or Firm*—Finnegan, Henderson, Farabow, Garrett & Dunner, L.L.P.

(57) ABSTRACT

A capacitor C and an impedance converter Hiz are included in a feedback circuit of the first operational amplifier $OP_1$ in series; an electrode $P_1$ of a capacitive sensor is connected to a connection point of the said capacitor and the converter via a signal line L. The signal line L is connected to a predetermined standard electric potential through resistance $R_3$ whose resistance value is high. When the capacitor is included in the feedback circuit, the signal line becomes in a state of floating and a circuit operation becomes unstable, however, the signal line L is fixed at predetermined electric potential, and therefore, the operation becomes stable. It is acceptable to configure the impedance converter with a voltage follower and connect the resistance $R_3$ to the output.

11 Claims, 3 Drawing Sheets

SENSOR CAPACITY SENSING APPARATUS AND SENSOR CAPACITY SENSING METHOD

TECHNICAL FIELD

This invention relates to detection technology of a sensor capacitance and particularly to a sensor capacitance apparatus and method that can fix electric potential of a connection line between a capacitive sensor and a detector to measure a very small capacitance precisely.

BACKGROUND ART

FIG. 1 shows a conventional example of a sensor capacitance measurement apparatus to measure a sensor capacitance in the case of electrostatic capacitance changing at various kinds of frequency such as a capacitor microphone. The said sensor capacitance measurement apparatus, as shown in FIG. 1, includes an operational amplifier OP equipped with a feedback resistance $R_f$, an AC voltage generator OSC that generates AC voltage $V_{in}$, a sensor capacitance $C_s$ is connected between an input terminal of the operation amplifier OP and the AC voltage generator OSC via a signal line L.

In the conventional sensor capacitance measurement apparatus shown in FIG. 1, electric current flows through the sensor capacitance $C_s$ by the AC voltage $V_{in}$ from the AC voltage generator OSC. Since the input impedance of the operational amplifier OP is ideally infinite and further two input terminals of the operational amplifier OP are in a state of imaginary short, the voltage $V_{out} = -(j\omega_{in} C_s) \cdot R_f V_{in}$ is outputted from a output terminal of the operational amplifier OP. By executing signal processing to the said output voltage $V_{out}$, it is possible to obtain a value corresponding to the sensor capacitance $C_s$.

The conventional sensor capacitance detection apparatus shown in FIG. 1 uses the resistance $R_f$ as feedback impedance. Assume that $V_{in} = V \cdot \sin \omega_{in} t$ and the sensor capacitance $C_s$ changes in response to applied physical quantity by angular frequency $\omega_c$ with a fixed standard capacitance $C_d$ at the center, namely, $C_s = C_d + \Delta C \cdot \sin \omega_c t$ and the output voltage $V_{out}$ can be represented as below.

$$V_{out} = -R_f[(C_d + \Delta C \cdot \sin \omega_c t) \cdot \omega_{in} \cdot \cos \omega_{in} t + \Delta C \cdot \omega_c \cdot \cos \omega_c t \cdot \sin \omega_{in} t] V \cdot \sin \omega_{in} t$$

As is apparent from this expression, the output voltage $V_{out}$ includes a term that is proportional to the angular frequency $\omega_c$ of the sensor capacitance and has frequency characteristics that depends on changing frequency of the sensor capacitance $C_s$.

Consequently, it is necessary to set up a processing circuit to cancel the term that is proportional to the said angular frequency $\omega_c$ at the subsequent stage of the sensor capacitance detection apparatus, and therefore, the size of overall apparatus becomes large.

Then, an apparatus that can obtain the output voltage $V_{out}$ that does not depend on the angular frequency $\omega_c$ of the sensor capacitance $C_s$ by substituting the feedback resistance of the operational amplifier OP for a feedback capacitor has been already proposed. FIG. 2 shows a sensor capacitance detection apparatus using the feedback capacitor $C_f$, and the output voltage $V_{out}$ of this apparatus can be represented as below.

$$V_{out} = -(C_d + \Delta C \cdot \sin \omega_c t)/C_f \cdot V \cdot \sin \omega_{in} t$$

As is apparent from this expression, since the output voltage $V_{out}$ does not have the changing frequency dependency of the sensor capacitance, an additional circuit to cancel the term that is proportional to an angular frequency $\omega_c$ component is not necessary.

Since the sensor capacitance detection apparatus shown in FIG. 2 uses the feedback capacitor $C_f$ as the feedback impedance of the operational amplifier, the electric current does not come in and out the signal line L that connects the said capacitor $C_f$ and the sensor capacitance $C_s$. Consequently, since the signal line L is in an electrically floating state, the electric potential becomes unstable, it happens that the circuit output is saturated with the power voltage and there is a problem that the circuit does not operate normally.

The present invention is done to solve the above-described problem of the conventional example and its object is to make it possible to fix the electric potential of the signal line even in the case of using a capacitor as the feedback circuit of the operational amplifier in the sensor capacitance detection circuit.

DISCLOSURE OF INVENTION

To achieve the above-mentioned objects, a sensor capacitance detection apparatus according to the present invention is a sensor capacitance detection apparatus that detects capacitance of a capacitive sensor whose capacitance changes in response to a change of physical quantity comprising: a voltage generator that supplies at least one of AC voltage or DC voltage; an operational amplifier; a capacitor; an impedance converter; a signal line of which one end can be connected to the capacitive sensor and the other terminal is connected to an input terminal of the impedance converter and the capacitor, respectively; a first resistance whose both ends are connected to the signal line and standard voltage, respectively; wherein an output terminal of the voltage generator is connected to an input terminal of the operational amplifier, and the capacitor and the impedance converter are included in a feedback loop of the operational amplifier.

Here, the first resistance may be set up in order that there are nearly no inflow and outflow of electric current between the signal line and the first resistance or in order that when the capacitive sensor is connected to the signal line and capacitance of the capacitive sensor changes, impedance of the first resistance viewed from the signal line is higher than impedance of the feedback loop or the capacitive sensor viewed from the signal line.

Additionally, a sensor capacitance detection apparatus according to the present invention is a sensor capacitance detection apparatus that detects capacitance of a capacitive sensor whose capacitance changes in response to a change of physical quantity comprising: a voltage generator that supplies at least one of AC voltage or DC voltage; an operational amplifier; a capacitor; an impedance converter; a signal line of which one end can be connected to a capacitive sensor and the other terminal is connected to an input terminal of the impedance converter and the capacitor, respectively; a second resistance both ends of which are connected to the signal line and an output terminal of the impedance converter, respectively; wherein an output terminal of the voltage generator is connected to an input terminal of the operational amplifier, and the capacitor and the impedance converter are included in a feedback loop of the operational amplifier.

Here, the second resistance may be set up in order that there are nearly no inflow and outflow of electric current between the signal line and the second resistance or in order that when the capacitive sensor is connected to the signal line and capacitance of the capacitive sensor changes, impedance of the second resistance viewed from the signal line is higher than impedance of the feedback loop or the capacitive sensor viewed from the signal line.

Note that "when capacitance of a sensor changes" includes not only a change in frequency but everything that changes temporally, for example, what goes up and comes down smoothly and what rises instantaneously like a digital signal.

Furthermore, to achieve the above-mentioned objects, a sensor capacitance detection method according to the present invention is a sensor capacitance detection method for detecting capacitance of a capacitive sensor whose capacitance changes in response to a change of physical quantity including: a step for connecting one end of a capacitive sensor and one end of a resistance to a connection point of a capacitor and an impedance converter that are included in a feedback loop of an operational amplifier in series; a step for applying at least one of AC voltage or DC voltage into the operational amplifier; a step for outputting output voltage in response to a sensor capacitance from an output terminal of the operational amplifier, wherein impedance of the resistance viewed from the signal line is set up to be higher than impedance of the feedback loop or the capacitive sensor viewed from the signal line when capacitance of the capacitive sensor changes.

Here, the present invention may be a sensor capacitance detection method for detecting capacitance of a capacitive sensor whose capacitance changes in response to a change of physical quantity including: a step for connecting one end of a capacitive sensor and one end of a resistance to a connection point of a capacitor and an impedance converter that are inserted to a feedback loop of an operational amplifier in series; a step for applying at least one of AC voltage or DC voltage into the operational amplifier; a step for outputting output voltage that corresponds to a sensor capacitance from an output terminal of the operational amplifier, wherein an electric current is made nearly zero between the signal line and the resistance when capacitance of the capacitive sensor changes.

BEST MODE FOR CARRYING OUT THE INVENTION

Figure 1:
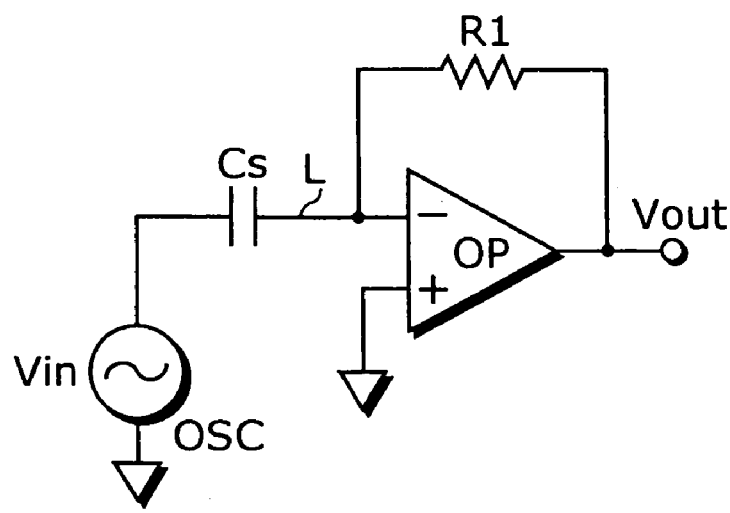
FIG. 1 is a circuit diagram that shows a conventional example of a sensor capacitance detection apparatus.
Figure 2:
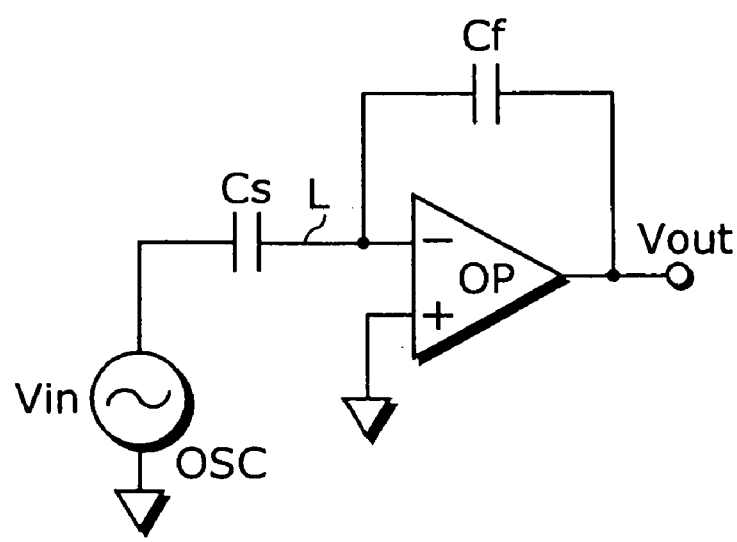
FIG. 2 is a circuit diagram that shows another conventional example of a sensor capacitance detection apparatus.
Figure 3:
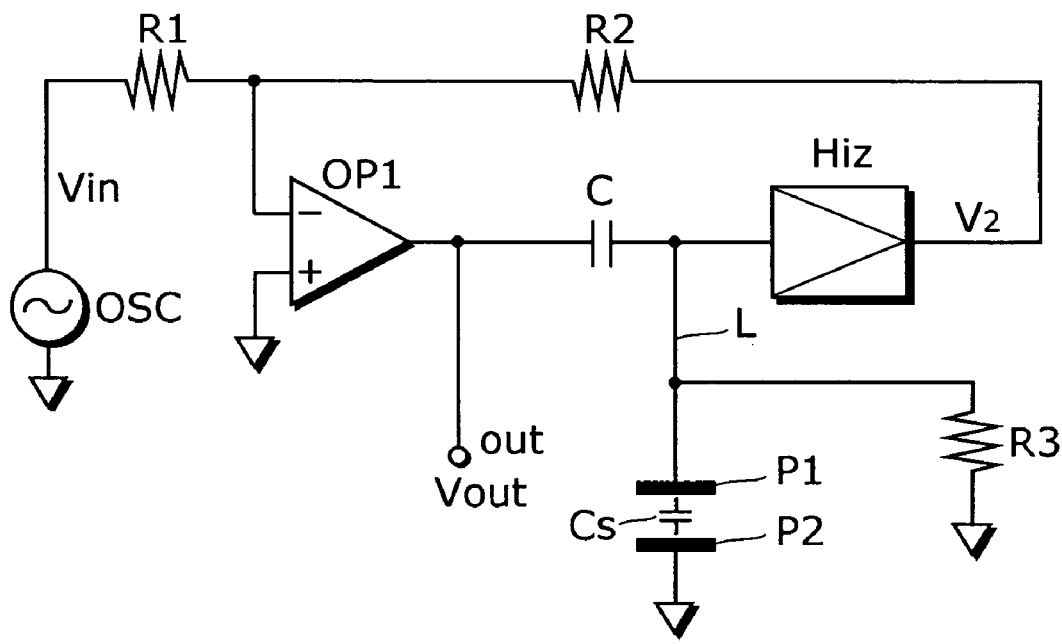
FIG. 3 is a circuit diagram that shows a sensor capacitance detection apparatus according to the first embodiment of the present invention.
Figure 5:
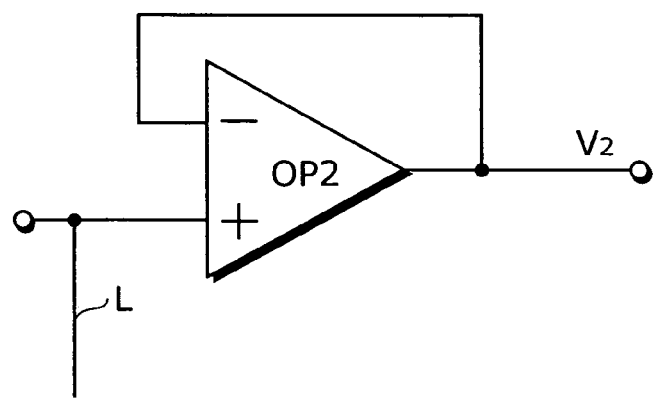
FIG. 5 is a circuit diagram that shows the concrete configuration of an impedance converter that the first embodiment shown in FIG. 3 equips.

FIG. 3 is a circuit diagram that shows the configuration of a sensor capacitance detection apparatus according to the first embodiment. The said sensor capacitance detection apparatus includes the first operational amplifier $OP_1$ and an impedance converter Hiz; an output terminal of the first operational amplifier $OP_1$ is connected to an input terminal of the impedance converter Hiz via the capacitor C. By the way, here, as shown in FIG. 5, an inversion input terminal and an output terminal of the second operational amplifier $OP_2$ are short-circuited and the impedance converter Hiz may be configured with a voltage follower circuit by this. The said voltage follower circuit makes a non-inversion input terminal an input terminal of the said circuit, is high input impedance and low output impedance, and the absolute value of input-output gain is 1. Now, the signal line L is further connected to an input terminal of the impedance converter Hiz; an electrode that forms one end of the capacitive sensor (an electrode of the sensor connection part) $P_1$ is connected to the other terminal of the said signal line L. In FIG. 3, the part of the signal line L is shown by thick solid lines. In addition, the sensor connection part is not illustrated. The electrode $P_2$ of the other terminal of the capacitive sensor is connected to standard electric potential, namely, predetermined electric potential. The standard electric potential may be ground electric potential. The electrode $P_2$ of the other terminal of the capacitive sensor may be in a floating state but it is possible to measure with high accuracy when it is connected to the standard electric potential.

The capacitive sensor is a capacitor microphone, a very small displacement capacitive sensor and so on, whose electrostatic capacitance between the electrodes $P_1$ and $P_2$, namely, the sensor capacitance $C_s$ changes in response to received physical quantity (acceleration, pressure, gas, light, sound wave and so on).

The non-inversion input terminal of the first operational amplifier $OP_1$ is connected to the standard electric potential (predetermined DC electric potential including ground electric potential); AC input voltage $V_{in}$ (angular frequency $\omega_{in}$) is applied to the inversion input terminal from the AC voltage generator OSC through the first resistance $R_1$. The AC voltage generator OSC is also connected to an input terminal of the impedance converter Hiz through the first resistance $R_1$ and the second resistance $R_2$. The output terminal of the first operational amplifier $OP_1$ is connected to the output terminal OUT of the sensor capacitance detection apparatus, and the output voltage $V_{out}$ is outputted from the said output terminal OUT.

The second resistance $R_2$, the capacitor C, and the impedance converter Hiz make up a feedback circuit of the first operational amplifier $OP_1$.

The signal line L is also connected to a terminal of the third resistance $R_3$; the other terminal of the said resistance $R_3$ is connected to the standard electric potential (the predetermined electric potential including the ground electric potential). The third resistance $R_3$ is set up in order that when the capacitive sensor is connected to the signal line L and the capacitance of the capacitive sensor changes, the impedance of the third resistance $R_3$ viewed from the signal line L is higher than the impedance of the feedback loop or the capacitive sensor viewed from the signal line L.

Figure 6:
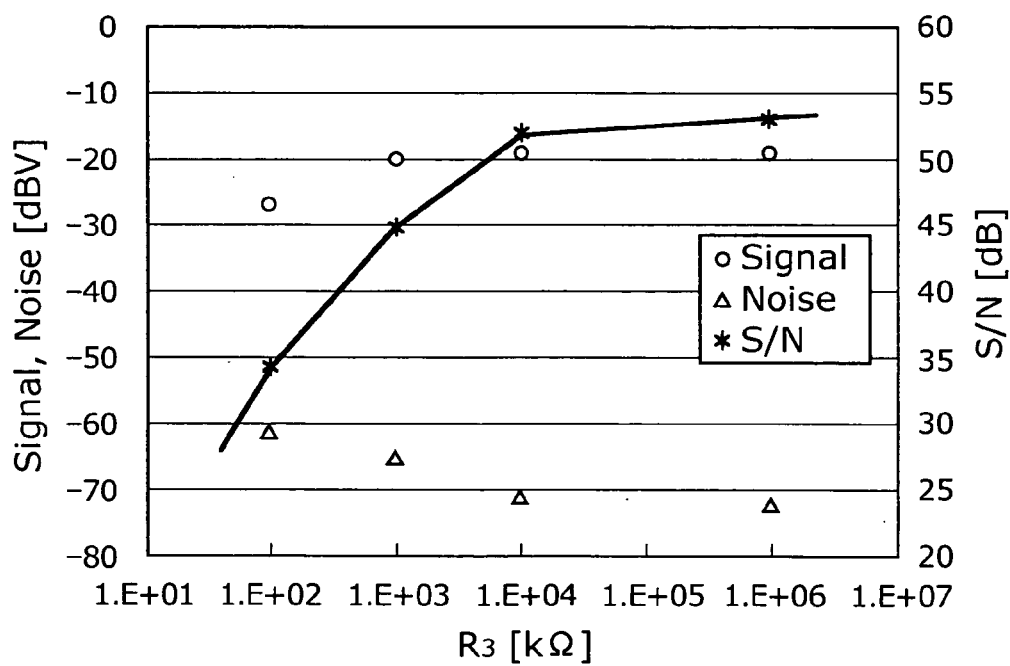
FIG. 6 is a graph that shows a result of an actual apparatus test executed using the sensor capacitance detection apparatus shown in FIG. 3.

FIG. 6 shows a result of an actual test executed using the sensor capacitance detection apparatus shown in FIG. 3. In this actual apparatus test, although the sensor capacitance $C_s$ changes in an audio frequency band (20 HZ~20 KHz), for example, the frequency is set at $f_c (=\omega_c/(2\pi))=1$ KHz and the first capacitor is set at C=0.5 pF. Then, the value of the third resistance $R_3$ is changed variously, signals and noises are measured, and S/N ratio is determined based on these measured values. As shown in FIG. 6, as a result of this actual apparatus test, it turns out that it is desirable to use resistance of 10 MΩ or more as the third resistance $R_3$.

However, since the S/N ratio changes in response to a time constant decided by a change frequency $f_c$ of the sensor capacitance $C_s$ and the capacitance of the first capacitor C, the value of the third resistance $R_3$ may be decided in response to the time constant. By the way, it is surmised experientially that the other frequencies by the above-mentioned actual apparatus test of the audio frequency band have a similar tendency.

By using a high resistance as the third resistance $R_3$, when an input terminal of the signal line L, namely, the impedance converter Hiz and the standard electric potential are connected through the said resistance, although electric potential difference between the both ends of the said resistance is generated, little or nothing of the AC that flows through the censor capacitance $C_s$ flows through the third resistance $R_3$ and it is in the state where the electric current does not come in and out.

Next, a detection operation of the sensor capacitance detection apparatus according to the first embodiment shown in FIG. 3 is explained. Note that in the following, an explanation is made assuming that the non-inversion input terminal of the first operational amplifier $OP_1$, an electrode $P_2$ of the capacitive sensor and one terminal of the AC voltage generator OSC are connected to ground and the voltage follower whose configuration shown in FIG. 5 is used.

(Detection of the Sensor Capacitance)

By the first operational amplifier $OP_1$ and the second operation amplifier $OP_2$, and the first resistance $R_1$ and the second resistance $R_2$, at the output terminal of the second operational amplifier $OP_2$, voltage $V_2$ that is $(-R_2/R_1)$ times of the AC input voltage $V_{in}$ is obtained. Namely, $$V_2 = -R_2/R_1 \cdot V_{in} \tag{1}$$

On the other hand, as for the AC that flows via the sensor capacitance $C_s$, since the input impedance of the second operational amplifier $OP_2$ is high and the output impedance of an electric potential fixing circuit is high, almost all the electric current flows through the capacitor C. In other words, the electric current does not come in and out between the resistance $R_3$ of the electric potential fixing circuit and the signal line L. Additionally, since two input terminals of the second operational amplifier $OP_2$ are in the state of imaginary short and have the same electric potential, the voltage of the non-inversion input terminal of the second operational amplifier $OP_2$ is also $V_2$; assume that $V_{in} = V \cdot \sin \omega_{in} t$ and the electric current that flows through the sensor capacitance $C_s$ is $$I_s = dC_s \cdot V_2/dt \tag{2}$$

Consequently, from the expression (1)

$$I_s = -(R_2/R_1) \cdot dC_s \cdot V_{in} \sin \omega_{in} t/dt \tag{3}$$

is obtained.

On the other hand, the electric current $I_c$ is $$I_c = dC(V_{out} - V_2)/dt \tag{4}$$

Since the electric current $I_c$ that flows through the capacitor C and $I_s$ that flows through the sensor capacitance $C_s$ are equal, from the expressions (3) and (4), the output voltage $V_{out}$ of the output terminal OUT can be represented by $$V_{out} = -(R_2/R_1) \cdot (1 + C_s/C) \cdot V \cdot \sin \omega_{in} t \tag{5}$$

As is apparent from the expression (5), the output voltage $V_{out}$ has a linear relationship with the sensor capacitance $C_s$ and therefore the value of the sensor capacitance $C_s$ can be obtained by executing signal processing to the said output voltage $V_{out}$.

(Detection of a Change Part of the Sensor Capacitance)

Next, like a capacitor microphone and so on, the detection of the change part $\Delta C$ in the case of the sensor capacitance $C_s$ changing at the angular frequency $\omega_c$ with a certain capacitance value $C_d$ at the center, in other words, the detection of the change part $\Delta C$ in the case of $$C_s = C_d + \Delta C \sin \omega_c$$

is explained.

As is described above, all the electric current i that flows through the first capacitor C flows through the sensor capacitance $C_s$ and therefore the electric charge stored in the sensor capacitance $C_s$ and the electric charge stored in the first capacitor C are equal.

$$C(V_{out} - V_2) = C_s \cdot V_2 \tag{6}$$

When the expression (6) is transformed, $V_{in} = V \cdot \sin \omega_{in} t$ and therefore the following expression (7) is obtained.

$$V_{out} = (-R_2/R_1) \cdot (1 + C_s/C) \cdot V \cdot \sin \omega_{in} t \tag{7}$$
$$= (-R_2/R_1) \cdot V \cdot \sin \omega_{in} t (1 + C_d/C +$$
$$\Delta C \cdot \sin \omega_c t/C)$$

As described above, since the output voltage $V_{out}$ does not have dependency on the change frequency of the sensor capacitance $C_s$, the output that depends on the change part $\Delta C$ of the sensor $C_s$ linearly can be obtained.

Figure 4:
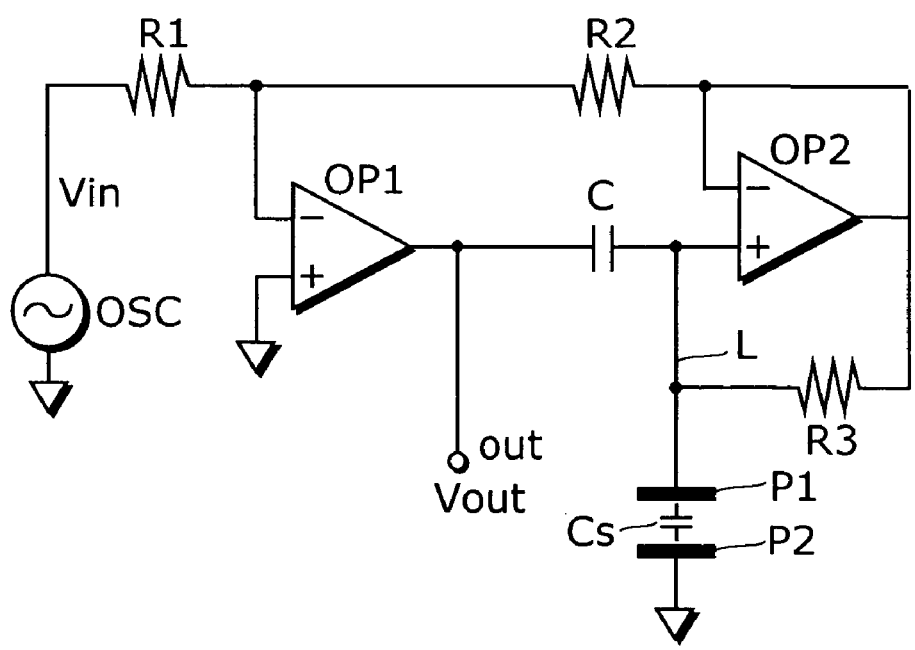
FIG. 4 is a circuit diagram that shows a sensor capacitance detection apparatus according to the second embodiment of the present invention.

In the embodiment shown in FIG. 3, the third resistance $R_3$ to fix the electric potential of the signal line is connected to the standard electric potential (predetermined electric potential including zero electric potential) but in the case of using what is shown in FIG. 5 as an impedance converter, the third resistance $R_3$ may be connected to the output terminal of the second operational amplifier $OP_2$ instead of the standard electric potential. FIG. 4 shows the second embodiment in the case of connecting the third resistance $R_3$ that is a high resistance to the signal line L and the output terminal of the second operational amplifier $OP_2$ like this.

In this second embodiment, the signal line L is fixed to electric potential decided by the electric potential of the AC voltage $V_{in}$ and non-inversion input terminal. Additionally, since the third resistance $R_3$ is connected between the inversion input terminal and the non-inversion input terminal of the second operational amplifier $OP_2$ and these two input terminals are in the state of imaginary short and ideally the same electric potential, there is no electric potential difference between the both ends of the third resistance $R_3$ and the electric current that flows is zero. Consequently, all the electric current that flows through the sensor capacitance $C_s$ flows through the capacitor C, the electric current does not come in and out between the signal line L and the third resistance $R_3$ and therefore the capacitance detection with higher accuracy can be realized.

In the first and the second embodiments, electric elements such as a diode and a transistor may be used as the third resistance $R_3$. In the case of using the diode, it is suitable to use high impedance in a state of its reverse bias; in the case of using the transistor, it is suitable to use an high impedance in its off state.

Furthermore, in the first and second embodiments, the AC voltage generator OSC is used, but a DC voltage generator may be used. When DC voltage is V, if some kind of physical quantity is added to the capacitive sensor, the capacitance of the said capacitive sensor changes and the output $V_{out}$ also changes. Then, the expressions (5) and (7) are represented by the following expressions (5)' and (7)', respectively.

$$V_{out} = -(R_2/R_1) \cdot (1+C_s/C) \cdot V \quad (5)'$$

$$V_{out} = -(R_2/R_1) \cdot (1+C_d/C+\Delta C \cdot \sin \omega_c t/C) \cdot V \quad (7)'$$

Further, by wrapping a part or the entire signal line L with a shield line (not illustrated) to shield electrically, and by applying guard voltage of the same electric potential as the signal line to the said shield line, it is possible to reduce influence of stray capacitance formed between the signal line and the standard electric potential and further improve the S/N ratio of the output voltage.

The present invention, as it is configured as above, can avoid the floating state of the signal line and therefore stabilize the circuit operation by fixing the electric potential of the signal line that connects the capacitive sensor and the second operational amplifier at the predetermined standard electric potential through the predetermined resistance that is set up so that the impedance of the resistance viewed from the signal line is higher than the impedance of the feedback loop or the capacitive sensor viewed from the signal line when the capacitive sensor is connected to the signal line and the capacitance of the capacitive sensor changes.

Moreover, by connecting the resistance set up as above to fix the electric potential of the signal line, between the output terminal of the second operational amplifier and the signal line, it is possible to cause the electric current that flows through both of the said resistance and the signal line to be zero ideally and take more accurate capacitance measurement.

INDUSTRIAL APPLICABILITY

The sensor capacitance detection circuit according to the present invention can be used as a detection circuit of the capacitive sensor and particularly as a circuit for a microphone apparatus that small and light apparatus such as a capacitance measurement apparatus that takes a very small capacitance measurement precisely, and a cell phone.

What is claimed is:

1. A sensor capacitance detection apparatus that detects capacitance of a capacitive sensor whose capacitance changes in response to a change of physical quantity comprising:
   a voltage generator that supplies at least one of AC voltage and DC voltage;
   an operational amplifier;
   a capacitor;
   an impedance converter;
   a signal line one end of which is connected to the capacitive sensor and the other end of which is connected to an input terminal of the impedance converter and the capacitor, respectively;
   a first resistance one end of which is connected to the signal line and the other end of which is connected to standard voltage;
   wherein an output terminal of the voltage generator is connected to an input terminal of the operational amplifier, and
   the capacitor and the impedance converter are included in a feedback loop of the operational amplifier.

2. The sensor capacitance detection apparatus according to claim 1,
   wherein the first resistance is set up in order that there are nearly no inflow and outflow of electric current between the signal line and the first resistance.

3. The sensor capacitance detection apparatus according to claim 1,
   wherein the first resistance is set up in order that when the capacitive sensor is connected to the signal line and capacitance of the capacitive sensor changes, impedance of the first resistance viewed from the signal line is higher than impedance of the feedback loop or the capacitive sensor viewed from the signal line.

4. A sensor capacitance detection apparatus that detects capacitance of a capacitive sensor whose capacitance changes in response to a change of physical quantity comprising:
   a voltage generator that supplies at least one of AC voltage and DC voltage;
   an operational amplifier;
   a capacitor;
   an impedance converter;
   a signal line one end of which is connected to a capacitive sensor and the other end of which is connected to an input terminal of the impedance converter and the capacitor, respectively;
   a first resistance one end of which is connected to the signal line and the other end of which is connected to an output terminal of the impedance converter,
   wherein an output terminal of the voltage generator is connected to an input terminal of the operational amplifier, and
   the capacitor and the impedance converter are included in a feedback loop of the operational amplifier.

5. The sensor capacitance detection apparatus according to claim 4,
   wherein the first resistance is set up in order that there are nearly no inflow and outflow of electric current between the signal line and the first resistance.

6. The sensor capacitance detection apparatus according to the claim 4,
   wherein the first resistance is set up in order that when the capacitive sensor is connected to the signal line and capacitance of the capacitive sensor changes, impedance of the first resistance viewed from the signal line is higher than impedance of the feedback loop or the capacitive sensor viewed from the signal line.

7. The sensor capacitance detection apparatus according to any of claims 1 through 6,
   wherein the first resistance or the first resistance is 10 MΩ or more when a change frequency of capacitance of the capacitive sensor is an audio frequency band.

8. The sensor capacitance detection apparatus according to any of claims 1 through 6,
   wherein the impedance converter is formed by a voltage follower.

9. The sensor capacitance detection apparatus according to any of claims 1 through 6, further comprising:
   a shield unit operable to shield at least part of the signal line electrically; and
   a guard voltage applying unit operable to apply voltage that is same electric potential as voltage of the signal line to the shield unit.

10. A sensor capacitance detection method for detecting capacitance of a capacitive sensor whose capacitance changes in response to a change of physical quantity including:
    a step for connecting one end of a capacitive sensor and one end of a resistance to a connection point of a capacitor and an impedance converter that are included in a feedback loop of an operational amplifier in series;

a step for applying at least one of AC voltage and DC voltage into the operational amplifier;

a step for outputting output voltage in response to a sensor capacitance from an output terminal of the operational amplifier, wherein impedance of the resistance viewed from the signal line is set up to be higher than impedance of the feedback loop or the capacitive sensor viewed from the signal line when capacitance of the capacitive sensor changes.

11. A sensor capacitance detection method for detecting capacitance of a capacitive sensor whose capacitance changes in response to a change of physical quantity including:

a step for connecting one end of a capacitive sensor and one end of a resistance to a connection point of a capacitor and an impedance converter that are inserted to a feedback loop of an operational amplifier in series;

a step for applying at least one of AC voltage and DC voltage into the operational amplifier;

a step for outputting output voltage that corresponds to a sensor capacitance from an output terminal of the operational amplifier, wherein an electric current is made nearly zero between the signal line and the resistance when capacitance of the capacitive sensor changes.

* * * * *